United States Patent
Hunt et al.

(10) Patent No.: US 11,097,071 B1
(45) Date of Patent: Aug. 24, 2021

(54) TAMPER EVIDENT ASSEMBLY

(71) Applicants: Timothy Brandon Hunt, Ft. Lauderdale, FL (US); Patrick Vitello, Pompano Beach, FL (US); Robert Banik, Ft. Lauderdale, FL (US)

(72) Inventors: Timothy Brandon Hunt, Ft. Lauderdale, FL (US); Patrick Vitello, Pompano Beach, FL (US); Robert Banik, Ft. Lauderdale, FL (US)

(73) Assignee: INTERNATIONAL MEDICAL INDUSTRIES INC., Pompano Beach, FL (US)

( * ) Notice: Subject to any disclaimer, the term of this patent is extended or adjusted under 35 U.S.C. 154(b) by 641 days.

(21) Appl. No.: 15/842,328

(22) Filed: Dec. 14, 2017

Related U.S. Application Data

(60) Provisional application No. 62/434,240, filed on Dec. 14, 2016, provisional application No. 62/434,221, filed on Dec. 14, 2016.

(51) Int. Cl.
*A61M 5/50* (2006.01)
*B65B 7/28* (2006.01)
*A61M 5/31* (2006.01)

(52) U.S. Cl.
CPC ..... *A61M 5/5086* (2013.01); *A61M 2005/312* (2013.01); *A61M 2005/3104* (2013.01); *B65B 7/2835* (2013.01)

(58) Field of Classification Search
CPC ................. A61M 5/5086; A61M 5/50; A61M 2005/3104; A61M 2005/312;
(Continued)

(56) References Cited

U.S. PATENT DOCUMENTS 732,662 A 6/1903 Smith
1,678,991 A 7/1928 Marschalek
(Continued)

FOREIGN PATENT DOCUMENTS

EP 0148116 A 7/1985
GB 486367 6/1938
(Continued)

*Primary Examiner* — Jason E Flick
(74) *Attorney, Agent, or Firm* — Malloy and Malloy PL

(57) ABSTRACT

A tamper evident assembly for attachment to a medical connector including a tamper evident cap having an end cap and a tip cap movably and removably disposed in an operative position within the end cap. A retaining structure on the end cap and a retention structure on the tip cap are cooperatively structured to define an interruptive engagement and unidirectional passage of the retention structure over said retaining structure, when disposing the tip cap in the operative position. The interruptive engagement also defines an abutting engagement of said retaining structure with said retention structure, wherein the abutting engagement is preventative of passage of said retention structure over said retaining structure, concurrent to disposition of said tip cap out of said operative position. An included flow controller regulates fluid flow through a connector attached to the tamper evident cap and may establish a path of fluid flow with an attached conduit and the attached connector.

31 Claims, 10 Drawing Sheets

(58) Field of Classification Search
CPC .. A61M 2005/3117; A61M 2005/3118; A61M 39/20; A61M 2039/1061; B65B 7/2835
See application file for complete search history.

(56) References Cited

U.S. PATENT DOCUMENTS

| | | |
|---|---|---|
| 1,970,631 A | 8/1934 | Sherman |
| 2,477,598 A | 8/1949 | Hain |
| 2,739,590 A | 3/1956 | Yochem |
| 2,823,674 A | 2/1958 | Yochem |
| 2,834,346 A | 5/1958 | Adams |
| 2,875,761 A | 3/1959 | Helmer et al. |
| 2,888,015 A | 5/1959 | Hunt |
| 2,952,255 A | 9/1960 | Hein, Jr. |
| 3,122,280 A | 2/1964 | Goda |
| 3,245,567 A | 4/1966 | Knight |
| 3,323,798 A | 6/1967 | Miller |
| 3,364,890 A | 1/1968 | Andersen |
| 3,368,673 A | 2/1968 | Cowley |
| 3,598,120 A | 8/1971 | Mass |
| 3,610,241 A | 10/1971 | LeMarie |
| 3,700,215 A | 10/1972 | Hardman et al. |
| 3,706,307 A | 12/1972 | Hasson |
| 3,712,749 A | 1/1973 | Roberts |
| 3,747,751 A | 7/1973 | Miller et al. |
| 3,872,867 A | 3/1975 | Killinger |
| 3,904,033 A | 9/1975 | Haerr |
| 3,905,375 A | 9/1975 | Toyama |
| 3,937,211 A | 2/1976 | Merten |
| 3,987,930 A | 10/1976 | Fuson |
| 4,005,739 A | 2/1977 | Winchell |
| 4,043,334 A | 8/1977 | Brown et al. |
| 4,046,145 A | 9/1977 | Choksi et al. |
| 4,068,696 A | 1/1978 | Winchell |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,271,972 A | 6/1981 | Thor |
| 4,286,591 A | 9/1981 | Raines |
| 4,286,640 A | 9/1981 | Knox et al. |
| 4,313,539 A | 2/1982 | Raines |
| 4,369,781 A | 1/1983 | Gilson et al. |
| 4,420,085 A | 12/1983 | Wilson et al. |
| 4,430,077 A | 2/1984 | Mittleman et al. |
| 4,457,445 A | 7/1984 | Hanks et al. |
| 4,482,071 A | 11/1984 | Ishiwatari |
| D277,783 S | 2/1985 | Beck |
| 4,521,237 A | 6/1985 | Logothetis |
| 4,530,697 A | 7/1985 | Kuhlemann et al. |
| 4,571,242 A | 2/1986 | Klein et al. |
| 4,589,171 A | 5/1986 | McGill |
| 4,664,259 A | 5/1987 | Landis |
| 4,667,837 A | 5/1987 | Vitello et al. |
| 4,676,530 A | 6/1987 | Nordgren et al. |
| 4,693,707 A | 9/1987 | Dye |
| 4,726,483 A | 2/1988 | Drozd |
| 4,743,229 A | 5/1988 | Chu |
| 4,743,231 A | 5/1988 | Kay et al. |
| 4,760,847 A | 8/1988 | Vaillancourt |
| 4,813,564 A | 3/1989 | Cooper et al. |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 4,936,445 A | 6/1990 | Grabenkort |
| 5,009,323 A | 4/1991 | Montgomery et al. |
| 5,049,129 A | 9/1991 | Zdeb et al. |
| 5,057,093 A | 10/1991 | Clegg et al. |
| D323,392 S | 1/1992 | Byrne |
| 5,085,332 A | 2/1992 | Gettig et al. |
| 5,135,496 A | 8/1992 | Vetter et al. |
| 5,165,560 A | 11/1992 | Enniss, III et al. |
| 5,230,429 A | 7/1993 | Etheredge, III |
| 5,267,983 A | 12/1993 | Oilschlager et al. |
| 5,292,308 A | 3/1994 | Ryan |
| 5,293,993 A | 3/1994 | Yates, Jr. et al. |
| 5,295,599 A | 3/1994 | Smith |
| 5,312,367 A | 5/1994 | Nathan |
| 5,312,368 A | 5/1994 | Haynes |
| 5,328,466 A | 7/1994 | Denmark |
| 5,328,474 A | 7/1994 | Raines |
| 5,356,380 A | 10/1994 | Hoekwater et al. |
| 5,380,295 A | 1/1995 | Vacca |
| 5,405,339 A | 4/1995 | Kohnen et al. |
| 5,456,668 A | 10/1995 | Ogle, II |
| 5,458,580 A | 10/1995 | Hajishoreh |
| 5,468,224 A | 11/1995 | Souryal |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,624,402 A | 4/1997 | Imbert |
| 5,674,209 A | 10/1997 | Yarger |
| 5,695,470 A | 12/1997 | Roussigne et al. |
| 5,700,247 A | 12/1997 | Grimard et al. |
| 5,702,374 A | 12/1997 | Johnson |
| 5,713,485 A | 2/1998 | Liff et al. |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| D402,766 S | 12/1998 | Smith et al. |
| 5,883,806 A | 3/1999 | Meador et al. |
| 5,884,457 A | 3/1999 | Ortiz et al. |
| 5,902,269 A | 5/1999 | Jentzen |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,957,314 A | 9/1999 | Nishida et al. |
| 5,963,136 A | 10/1999 | O'Brien |
| 5,989,227 A | 11/1999 | Vetter et al. |
| 5,993,437 A | 11/1999 | Raoz |
| 6,000,548 A | 12/1999 | Tsals |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| D431,864 S | 10/2000 | Jansen |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,235,376 B1 | 5/2001 | Miyazaki et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,375,640 B1 | 4/2002 | Teraoka |
| 6,394,983 B1 | 5/2002 | Mayoral et al. |
| 6,485,460 B2 | 11/2002 | Eakins et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. |
| 6,682,798 B1 | 1/2004 | Kiraly |
| 6,726,652 B2 | 4/2004 | Eakins et al. |
| 6,726,672 B1 | 4/2004 | Hanley et al. |
| 6,755,220 B2 | 6/2004 | Castellano et al. |
| 6,764,469 B2 | 7/2004 | Broselow |
| 6,796,586 B2 | 9/2004 | Werth |
| 6,821,268 B2 | 11/2004 | Balestracci |
| D501,549 S | 2/2005 | McAllister et al. |

(56) References Cited

U.S. PATENT DOCUMENTS

| | | | |
|---|---|---|---|
| 6,921,383 B2 | 7/2005 | Vitello | |
| 6,935,560 B2 | 8/2005 | Andreasson et al. | |
| 6,942,643 B2 | 9/2005 | Eakins et al. | |
| 7,055,273 B2 | 6/2006 | Roshkoff | |
| 7,125,397 B2 | 10/2006 | Woehr et al. | |
| 7,141,286 B1 | 11/2006 | Kessler et al. | |
| 7,175,081 B2 | 2/2007 | Andreasson et al. | |
| 7,182,256 B2 | 2/2007 | Andreasson et al. | |
| 7,232,066 B2 | 6/2007 | Andreasson et al. | |
| 7,240,926 B2 | 7/2007 | Dalle et al. | |
| 7,299,981 B2 | 11/2007 | Hickle et al. | |
| 7,374,555 B2 | 5/2008 | Heinz et al. | |
| 7,404,500 B2 | 7/2008 | Marteau et al. | |
| 7,410,803 B2 | 8/2008 | Nollert et al. | |
| 7,425,208 B1 | 9/2008 | Vitello | |
| 7,437,972 B2 | 10/2008 | Yeager | |
| 7,482,166 B2 | 1/2009 | Nollert et al. | |
| 7,503,453 B2 | 3/2009 | Cronin et al. | |
| 7,588,563 B2 | 9/2009 | Guala | |
| 7,594,681 B2 | 9/2009 | DeCarlo | |
| 7,608,057 B2 | 10/2009 | Woehr et al. | |
| 7,611,487 B2 | 11/2009 | Woehr et al. | |
| 7,632,244 B2 | 12/2009 | Buehler et al. | |
| D608,900 S | 1/2010 | Giraud et al. | |
| 7,641,636 B2 | 1/2010 | Moesli et al. | |
| D612,939 S | 3/2010 | Boone, III et al. | |
| 7,681,606 B2 | 3/2010 | Khan et al. | |
| 7,698,180 B2 | 4/2010 | Fago et al. | |
| 7,735,664 B1 | 6/2010 | Peters et al. | |
| 7,748,892 B2 | 7/2010 | McCoy | |
| 7,762,988 B1 | 7/2010 | Vitello | |
| 7,766,919 B2 | 8/2010 | Delmotte | |
| 7,802,313 B2 | 9/2010 | Czajka | |
| 7,918,830 B2 | 4/2011 | Langan et al. | |
| 7,922,213 B2 | 4/2011 | Werth | |
| 8,034,041 B2 | 10/2011 | Domkowski | |
| 8,079,518 B2 | 12/2011 | Turner et al. | |
| 8,091,727 B2 | 1/2012 | Domkowski | |
| 8,118,788 B2 * | 2/2012 | Frezza | A61M 5/5086 604/200 |
| 8,137,324 B2 | 3/2012 | Bobst | |
| 8,140,349 B2 | 3/2012 | Hanson et al. | |
| 8,252,247 B2 | 8/2012 | Ferlic | |
| 8,257,286 B2 | 9/2012 | Meyer et al. | |
| 8,328,082 B1 | 12/2012 | Bochenko et al. | |
| 8,348,895 B1 | 1/2013 | Vitello | |
| 8,353,869 B2 | 1/2013 | Ranalletta et al. | |
| 8,443,999 B1 | 5/2013 | Reinders | |
| D684,057 S | 6/2013 | Kwon | |
| 8,512,277 B2 | 8/2013 | Del Vecchio | |
| 8,556,074 B2 | 10/2013 | Turner et al. | |
| 8,579,116 B2 | 11/2013 | Pether et al. | |
| 8,591,462 B1 | 11/2013 | Vitello | |
| 8,597,255 B2 | 12/2013 | Emmott et al. | |
| 8,597,271 B2 | 12/2013 | Langan et al. | |
| 8,616,413 B2 | 12/2013 | Koyama | |
| D701,304 S | 3/2014 | Lair et al. | |
| 8,672,902 B2 | 3/2014 | Ruan et al. | |
| 8,702,674 B2 | 4/2014 | Bochenko | |
| 8,777,910 B2 | 7/2014 | Bauss et al. | |
| 8,777,930 B2 | 7/2014 | Swisher et al. | |
| 8,852,561 B2 | 10/2014 | Wagner et al. | |
| 8,864,021 B1 | 10/2014 | Vitello | |
| 8,864,707 B1 | 10/2014 | Vitello | |
| 8,864,708 B1 | 10/2014 | Vitello | |
| 8,911,424 B2 | 12/2014 | Weadock et al. | |
| 8,945,082 B2 | 2/2015 | Geiger et al. | |
| 9,082,157 B2 | 7/2015 | Gibson | |
| 9,101,534 B2 | 8/2015 | Bochenko | |
| D738,495 S | 9/2015 | Strong et al. | |
| D743,019 S | 11/2015 | Schultz | |
| 9,199,042 B2 | 12/2015 | Farrar et al. | |
| 9,199,749 B1 | 12/2015 | Vitello | |
| 9,220,486 B2 | 12/2015 | Schweiss et al. | |
| 9,220,577 B2 | 12/2015 | Jessop et al. | |
| 9,227,019 B2 | 1/2016 | Swift et al. | |
| D750,228 S | 2/2016 | Strong et al. | |
| 9,272,099 B2 | 3/2016 | Limaye et al. | |
| 9,311,592 B1 | 4/2016 | Vitello et al. | |
| D756,777 S | 5/2016 | Berge et al. | |
| 9,336,669 B2 | 5/2016 | Bowden et al. | |
| D759,486 S | 6/2016 | Ingram et al. | |
| D760,384 S | 6/2016 | Niunoya et al. | |
| D760,902 S | 7/2016 | Persson | |
| 9,402,967 B1 | 8/2016 | Vitello | |
| 9,427,715 B2 | 8/2016 | Palazzolo et al. | |
| 9,433,768 B2 | 9/2016 | Tekeste et al. | |
| 9,463,310 B1 | 10/2016 | Vitello | |
| D773,043 S | 11/2016 | Insgram et al. | |
| D777,903 S | 3/2017 | Schultz | |
| 9,662,456 B2 | 5/2017 | Woehr | |
| D789,529 S | 6/2017 | Davis et al. | |
| 9,687,249 B2 | 6/2017 | Hanlon et al. | |
| 9,744,304 B2 | 8/2017 | Swift et al. | |
| D797,928 S | 9/2017 | Davis et al. | |
| D797,929 S | 9/2017 | Davis et al. | |
| 9,764,098 B2 | 9/2017 | Hund et al. | |
| 9,821,152 B1 | 11/2017 | Vitello et al. | |
| D806,241 S | 12/2017 | Swinney et al. | |
| D807,503 S | 1/2018 | Davis et al. | |
| 9,855,191 B1 | 1/2018 | Vitello et al. | |
| D815,945 S | 4/2018 | Fischer | |
| 9,987,438 B2 | 6/2018 | Stillson | |
| D825,746 S | 8/2018 | Davis et al. | |
| 10,039,913 B2 | 8/2018 | Yeh et al. | |
| D831,201 S | 10/2018 | Holtz et al. | |
| D820,187 S | 11/2018 | Ryan | |
| 10,124,122 B2 | 11/2018 | Zenker | |
| 10,166,343 B1 | 1/2019 | Hunt et al. | |
| 10,166,347 B1 | 1/2019 | Vitello | |
| 10,183,129 B1 | 1/2019 | Vitello | |
| 10,207,099 B1 | 2/2019 | Vitello | |
| D842,464 S | 3/2019 | Davis et al. | |
| D847,373 S | 4/2019 | Hurwit et al. | |
| 10,300,263 B1 | 5/2019 | Hunt | |
| 10,307,548 B1 | 6/2019 | Hunt et al. | |
| 10,315,024 B1 | 6/2019 | Vitello et al. | |
| 10,315,808 B2 | 6/2019 | Taylor et al. | |
| 10,376,655 B2 | 8/2019 | Pupke et al. | |
| D859,125 S | 9/2019 | Weagle et al. | |
| 10,758,684 B1 | 9/2020 | Vitello et al. | |
| 10,888,672 B1 | 1/2021 | Vitello | |
| 10,898,659 B1 | 1/2021 | Vitello et al. | |
| 10,912,898 B1 | 2/2021 | Vitello et al. | |
| 10,933,202 B1 | 3/2021 | Banik | |
| 10,953,162 B1 | 3/2021 | Hunt et al. | |
| 11,040,149 B1 | 6/2021 | Banik | |
| 11,040,154 B1 | 6/2021 | Vitello et al. | |
| 2001/0034506 A1 | 10/2001 | Hirschman et al. | |
| 2001/0056258 A1 | 12/2001 | Evans | |
| 2002/0007147 A1 | 1/2002 | Capes et al. | |
| 2002/0023409 A1 | 2/2002 | Py | |
| 2002/0097396 A1 | 7/2002 | Schafer | |
| 2002/0099334 A1 | 7/2002 | Hanson et al. | |
| 2002/0101656 A1 | 8/2002 | Blumenthal et al. | |
| 2002/0133119 A1 | 9/2002 | Eakins et al. | |
| 2003/0055685 A1 | 3/2003 | Cobb et al. | |
| 2003/0146617 A1 | 8/2003 | Franko, Sr. | |
| 2003/0183547 A1 | 10/2003 | Heyman | |
| 2004/0008123 A1 | 1/2004 | Carrender et al. | |
| 2004/0064095 A1 | 4/2004 | Vitello | |
| 2004/0116858 A1 | 6/2004 | Heinz et al. | |
| 2004/0186437 A1 | 9/2004 | Frenette et al. | |
| 2004/0225258 A1 | 11/2004 | Balestracci | |
| 2005/0146081 A1 | 7/2005 | MacLean et al. | |
| 2005/0148941 A1 | 7/2005 | Farrar et al. | |
| 2005/0209555 A1 | 9/2005 | Middleton et al. | |
| 2006/0084925 A1 | 4/2006 | Ramsahoye | |
| 2006/0089601 A1 | 4/2006 | Dionigi | |
| 2006/0173415 A1 | 8/2006 | Cummins | |
| 2006/0189933 A1 | 8/2006 | Alheidt et al. | |
| 2007/0060898 A1 | 3/2007 | Shaughnessy et al. | |
| 2007/0106234 A1 | 5/2007 | Klein | |
| 2007/0142786 A1 | 6/2007 | Lampropoulos et al. | |

(56) References Cited

U.S. PATENT DOCUMENTS

| | | |
|---|---|---|
| 2007/0191690 A1 | 8/2007 | Hasse et al. |
| 2007/0219503 A1 | 9/2007 | Loop et al. |
| 2007/0257111 A1 | 11/2007 | Ortenzi |
| 2008/0068178 A1 | 3/2008 | Meyer |
| 2008/0097310 A1 | 4/2008 | Buehler et al. |
| 2008/0106388 A1 | 5/2008 | Knight |
| 2008/0140020 A1 | 6/2008 | Shirley |
| 2008/0243088 A1 | 10/2008 | Evans |
| 2008/0306443 A1 | 12/2008 | Neer |
| 2009/0084804 A1 | 4/2009 | Caspary |
| 2009/0099552 A1 | 4/2009 | Levy et al. |
| 2009/0149815 A1 | 6/2009 | Kiel et al. |
| 2009/0166311 A1 | 7/2009 | Claessens |
| 2009/0326481 A1 | 12/2009 | Swisher et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0056130 A1 | 3/2013 | Alpert et al. |
| 2013/0088354 A1 | 4/2013 | Thomas |
| 2013/0237949 A1 | 4/2013 | Miller |
| 2013/0269592 A1 | 10/2013 | Heacock et al. |
| 2014/0000781 A1 | 1/2014 | Franko, Jr. |
| 2014/0034536 A1 | 2/2014 | Reinhardt et al. |
| 2014/0069202 A1 | 3/2014 | Fisk |
| 2014/0069829 A1 | 3/2014 | Evans |
| 2014/0135738 A1 | 5/2014 | Panian |
| 2014/0155868 A1 | 6/2014 | Nelson et al. |
| 2014/0163465 A1 | 6/2014 | Bartlett, II et al. |
| 2014/0257843 A1 | 9/2014 | Adler et al. |
| 2014/0326727 A1 | 11/2014 | Jouin et al. |
| 2014/0353196 A1 | 12/2014 | Key |
| 2015/0182686 A1 | 7/2015 | Okihara |
| 2015/0191633 A1 | 7/2015 | De Boer et al. |
| 2015/0305982 A1 | 10/2015 | Bochenko |
| 2015/0310771 A1 | 10/2015 | Atkinson et al. |
| 2016/0067422 A1 | 3/2016 | Davis et al. |
| 2016/0090456 A1 | 3/2016 | Ishimaru et al. |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Vitello et al. |
| 2016/0279032 A1 | 9/2016 | Davis |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0007771 A1 | 1/2017 | Duinat et al. |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0225843 A1 | 8/2017 | Glaser et al. |
| 2017/0239141 A1 | 8/2017 | Davis et al. |
| 2017/0319438 A1 | 11/2017 | Davis et al. |
| 2017/0354792 A1 | 12/2017 | Ward |
| 2018/0001540 A1 | 1/2018 | Byun |
| 2018/0078684 A1 | 3/2018 | Peng et al. |
| 2018/0089593 A1 | 3/2018 | Patel et al. |

FOREIGN PATENT DOCUMENTS

| | | |
|---|---|---|
| WO | WO2008/000279 | 1/2008 |
| WO | WO 2017086607 | 5/2015 |

\* cited by examiner

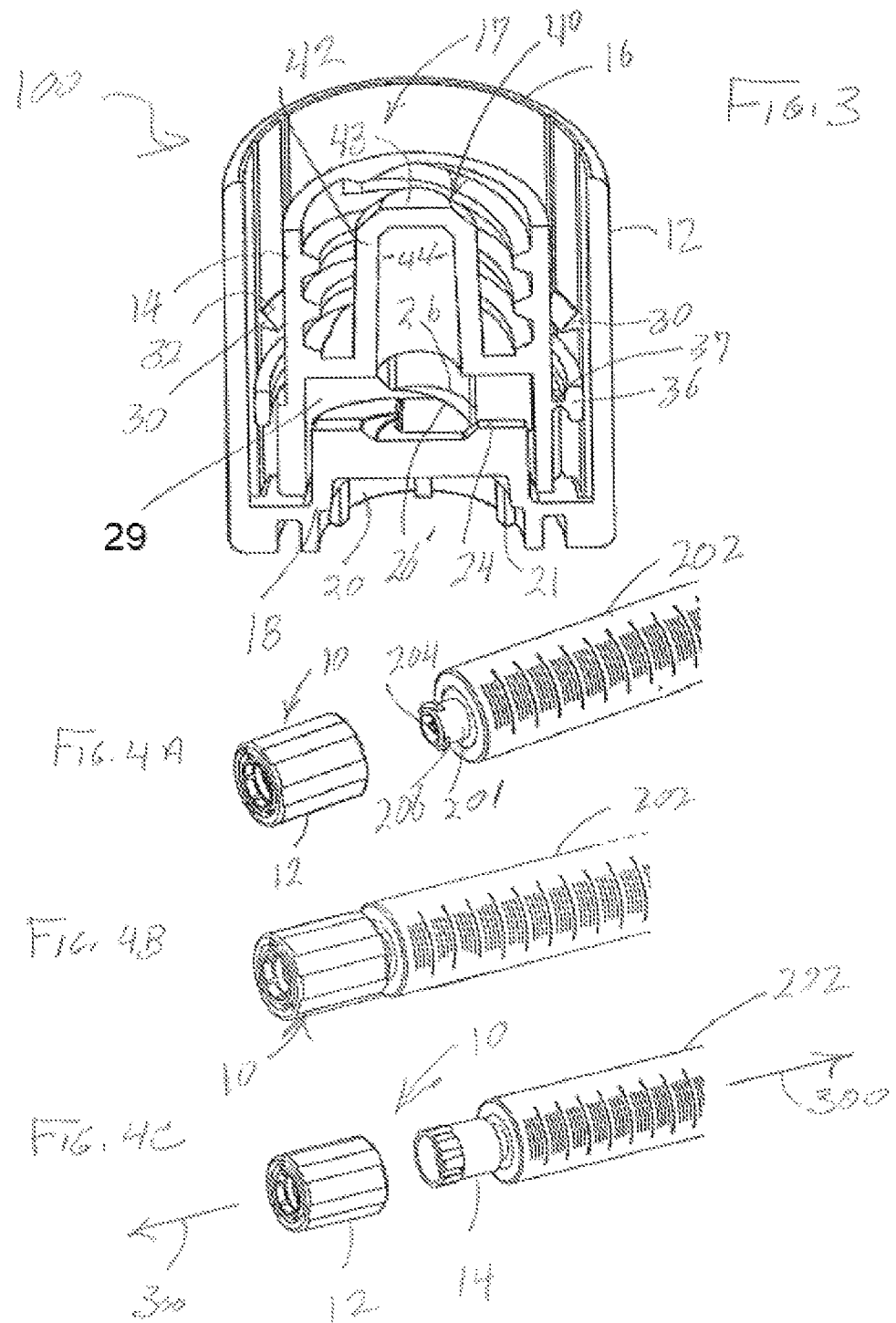

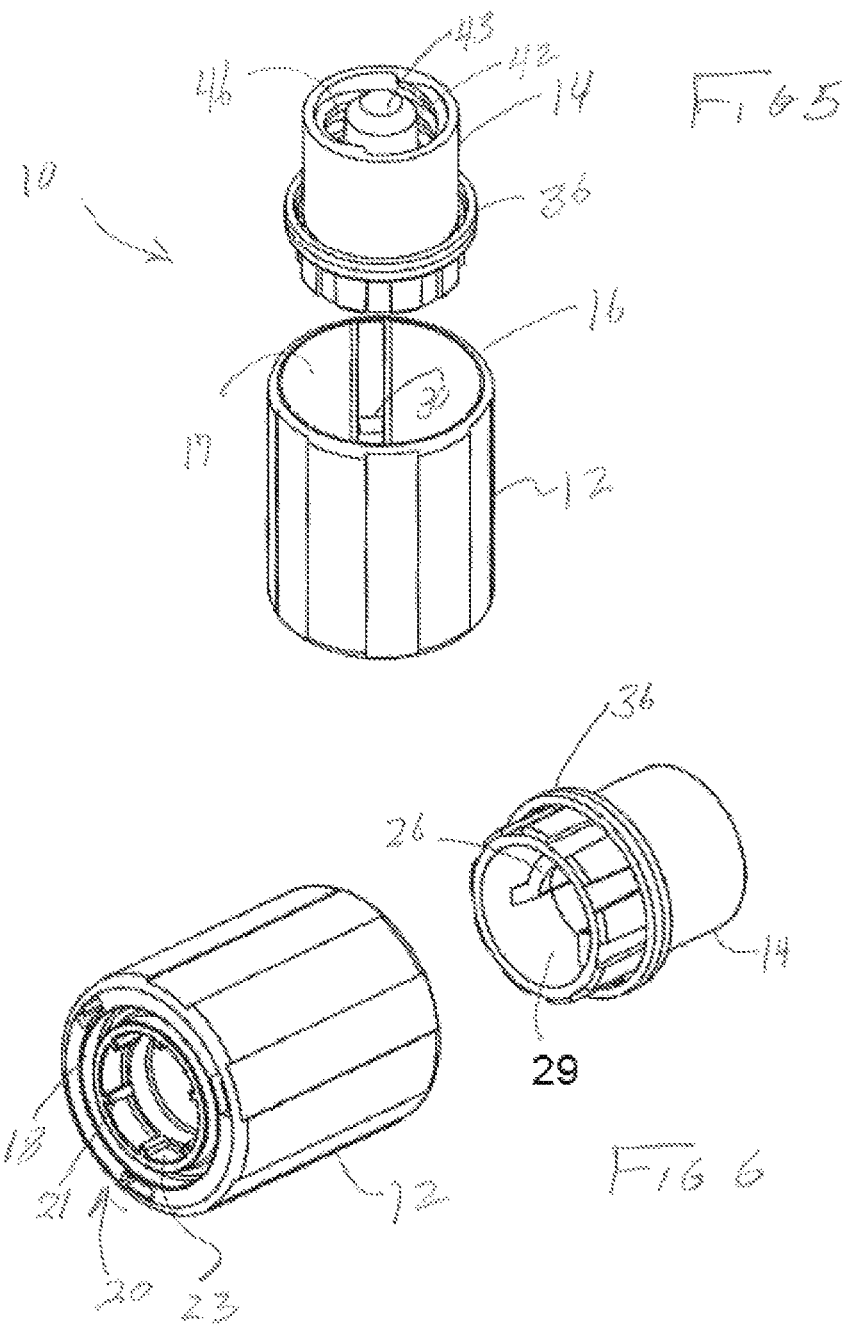

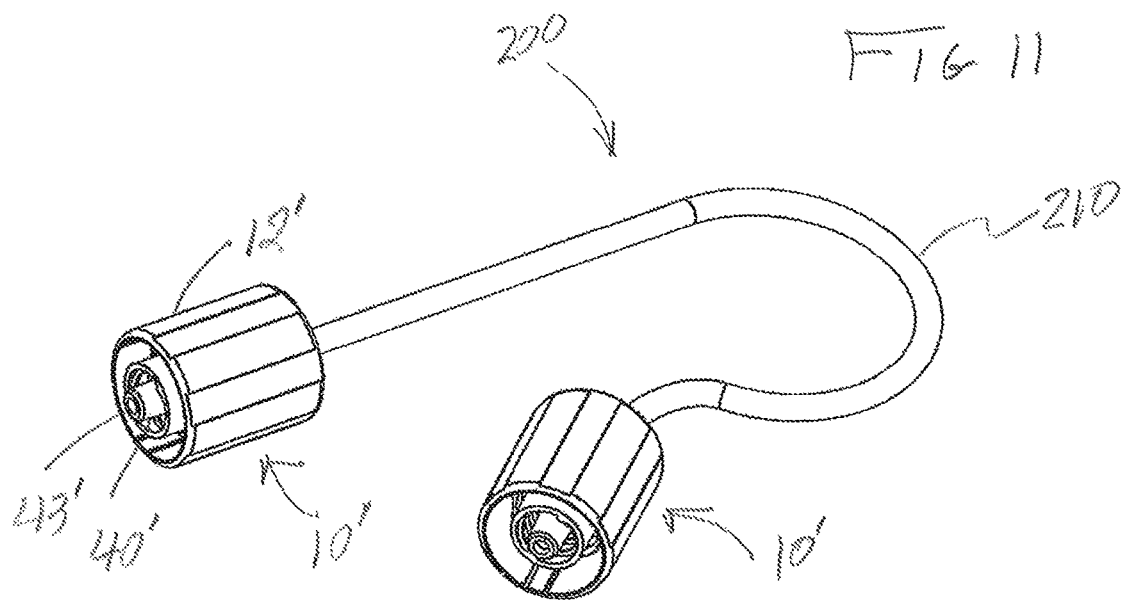
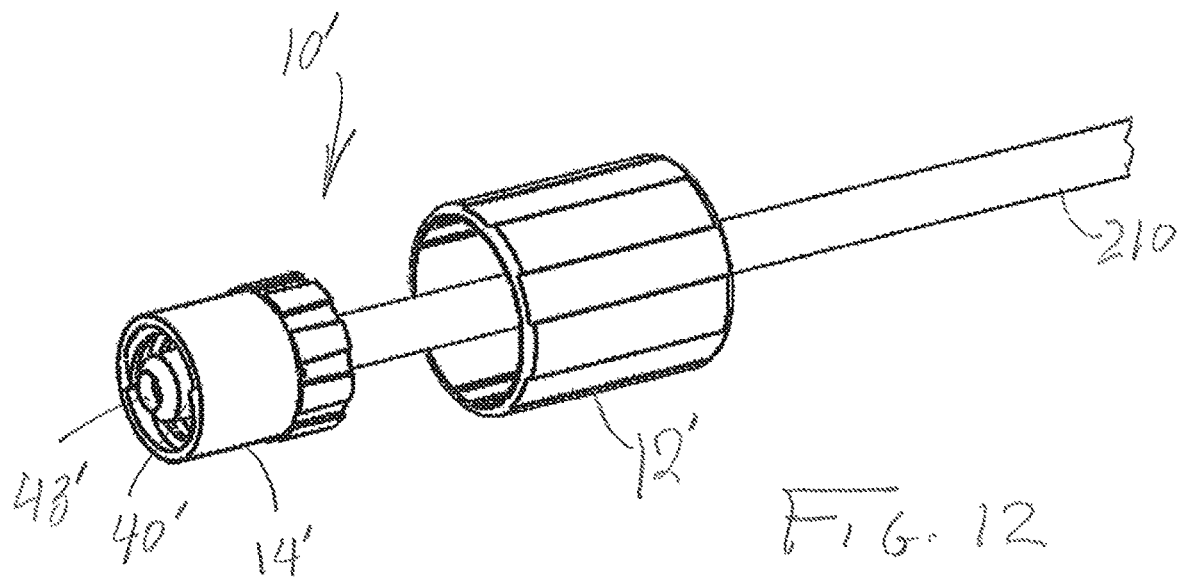

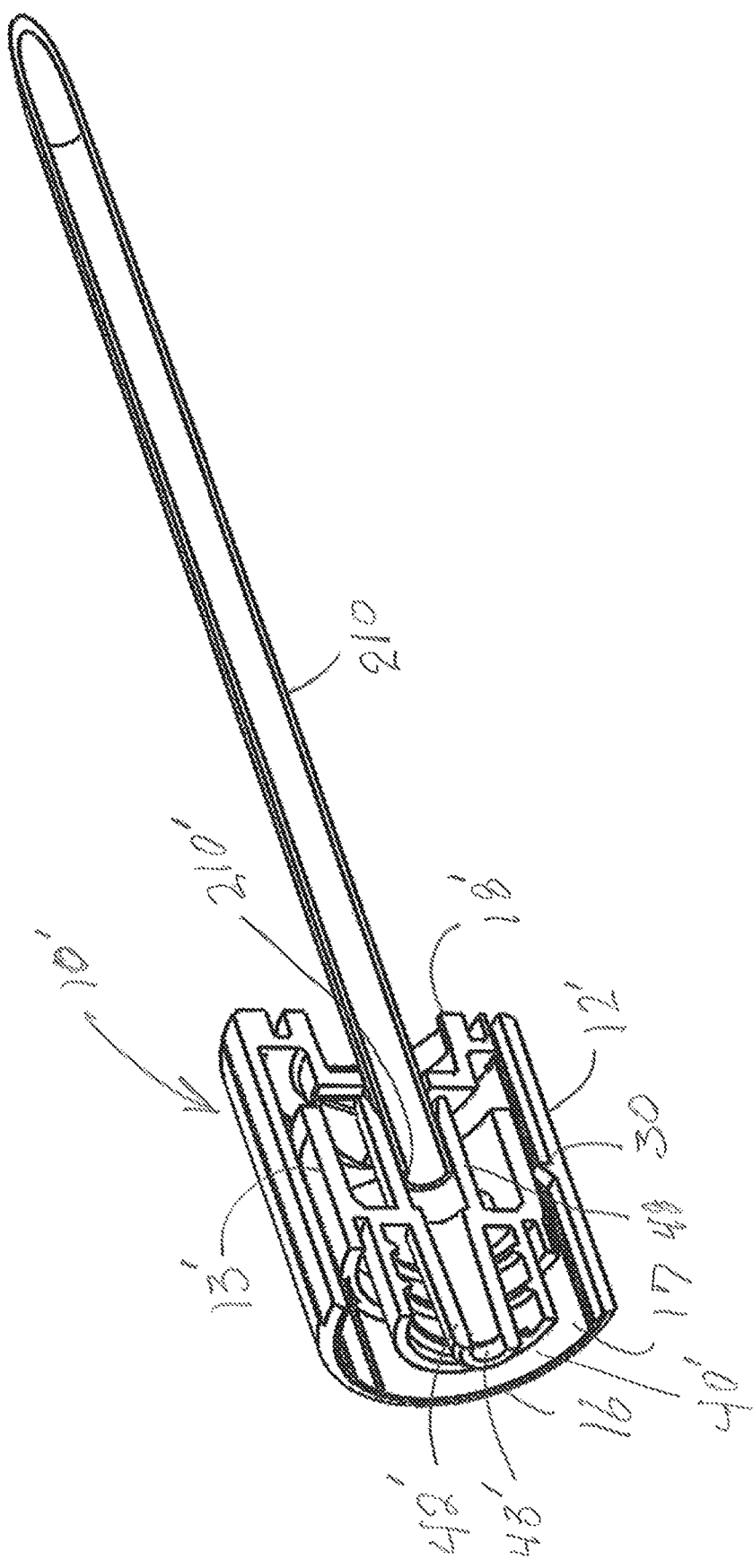

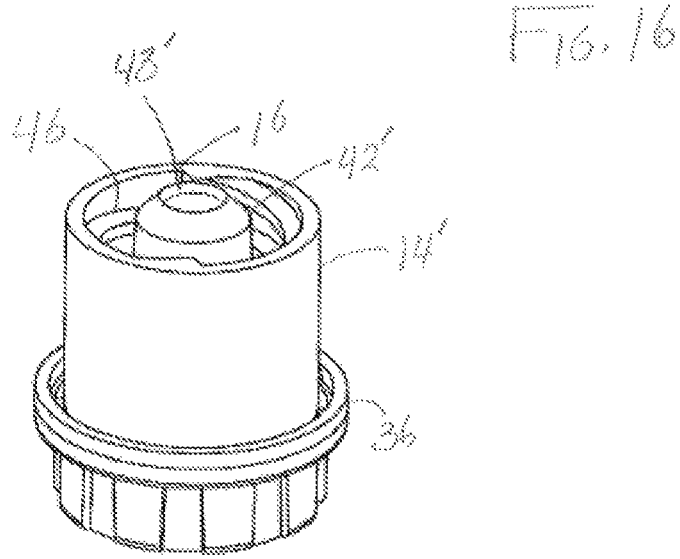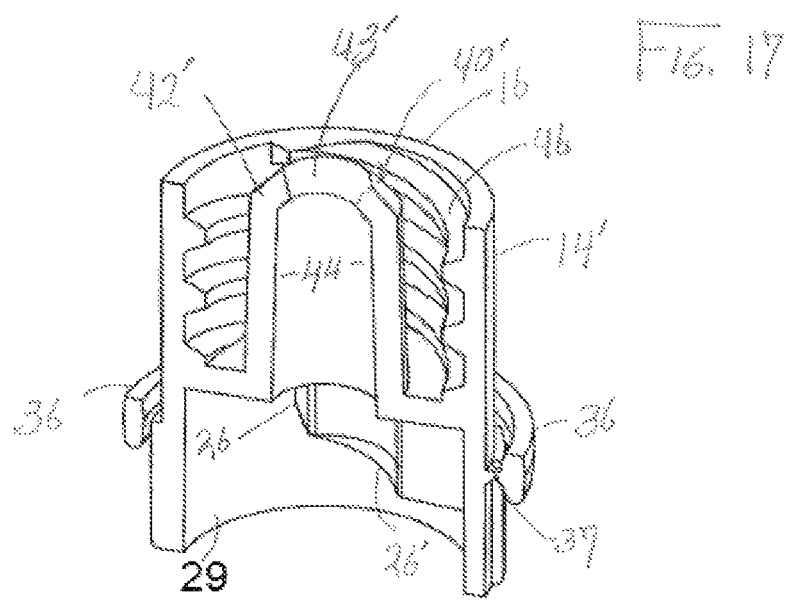

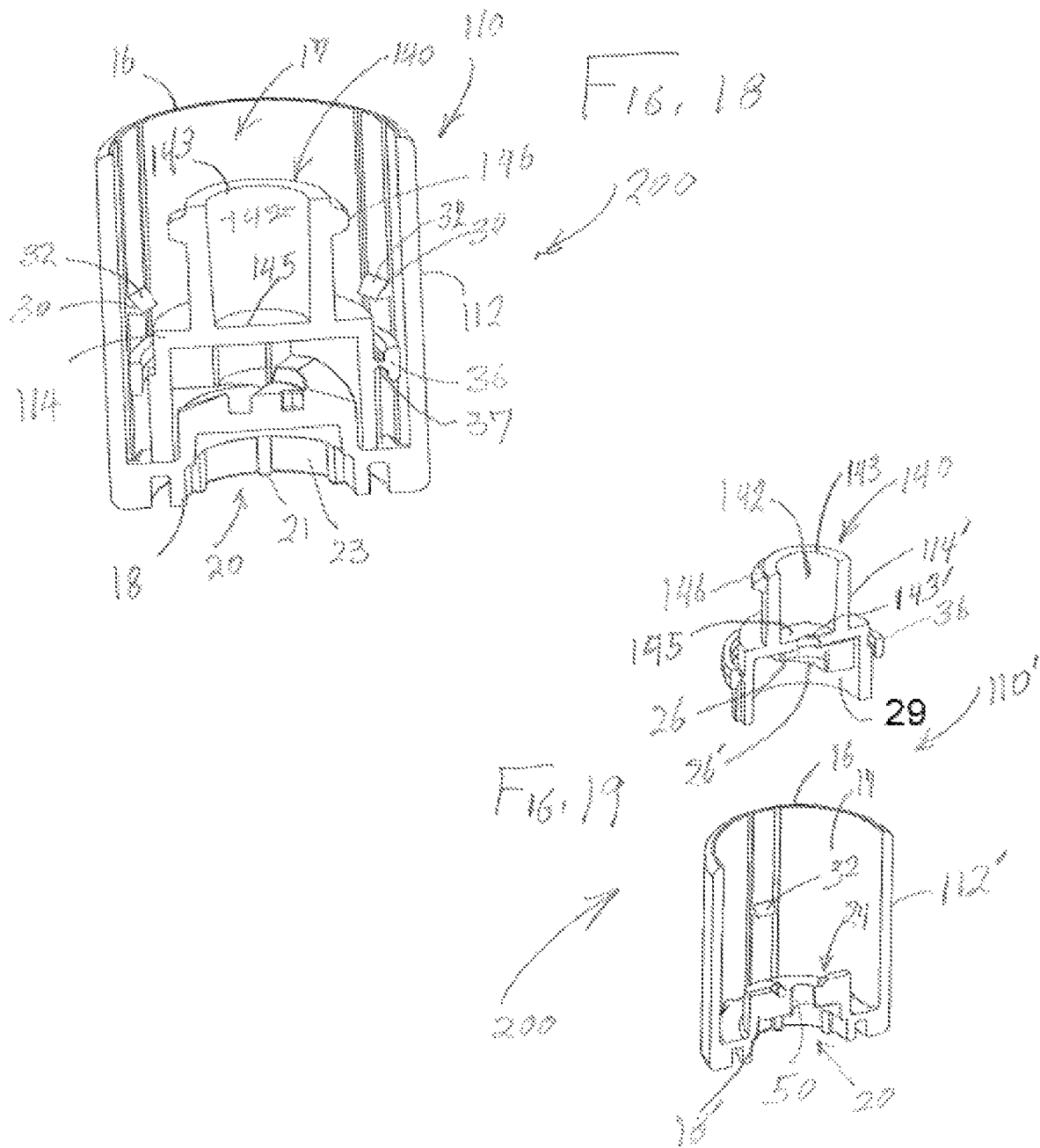

TAMPER EVIDENT ASSEMBLY

CLAIM OF PRIORITY

This Non-Provisional patent application claims priority to a U.S. provisional patent application having Ser. No. 62/434,221 and a filing date of Dec. 14, 2016, and also to another U.S. provisional patent application, namely, that having Ser. No. 62/434,240 and a filing date of Dec. 14, 2016, both of which are incorporated herein by reference in its entireties.

BACKGROUND OF THE INVENTION

Field of the Invention

This invention is directed to a tamper evident assembly including a tamper evident cap (TEC) which may be structured for attachment to either a male or female connector. Structural features of one or more embodiments of the TEC also facilitate its operative attachment to at least one open end of a medical tube, tube set, conduit, and the like.

Description of the Related Art

In the medical field, it is a relatively common procedure to administer fluids to patients using syringes, intravenous (IV) infusion devices, medical conduits, tube sets, etc. Such devices or assemblies are useful in the treatment of a number of medical conditions, in that a variety of fluids and/or medicines can be administered to a patient utilizing such assemblies over a prescribed period of time and in controlled amounts. During periods of non-use, however, it is typically very important to maintain such medical devices, including any connectors associated with them, in a closed and fluid-sealed condition, whether to maintain sterility or to assure the integrity of the any drug or fluid contained in such medical devices prior to use. It is also important in order to restrict unauthorized access to a drug or fluid, including access to any connector associated with the medical device.

By way of example, a conventional IV administration assembly typically includes a reservoir or container, in the form of a bottle or more commonly, a flexible material bag, suspended on a pole or a like support structure located substantially adjacent to the patient being treated, typically in an elevated relation thereto. In addition, the IV fluid flows from the supported and elevated IV bag to the patient by means of an elongated, flexible medical tubing or "tube set" connected at a proximal end to the IV bag and at the other distal end, connected intravenously to the patient by way of a catheter or like administrative device or structure.

In some situations, administration of fluids and/or a drug to a patient having an IV line and/or connection to an IV bag is done by means of a syringe that has been pre-filled with a prescribed fluid or drug. As set forth above, during periods of non-use, the medical devices such as an IV bag or other container, an IV line, a prefilled syringe, etc. and connectors associated with them, should be closed or sealed, while concurrently also being protected from non-authorized use.

Medical connectors associated with such medical devices may have a male or female configuration, dependent upon the structure and purpose of the medical device to which such connectors are secured. Accordingly, the medical connectors are structured to close or seal the contents of a given medical device, while also being structured to facilitate access thereto. More specifically, connectors of the type referred to may be in the form of a male or female connector attached to an IV bag, prefilled syringe, or other fluid container. Further, appropriate connectors of the type generally described above may be male or female Luer connectors, or another connector structured to be threadedly or otherwise removably attached. Further by way of example, a female connector may be secured to an IV delivery tubing, such as at the proximal end, and is structured to be attached to a male connector in a manner which establishes fluid communication with contents of the IV container. Once fluid communication is established, the flow of the IV fluid from the IV container or the contents of a prefilled syringe is facilitated through the attached male and female connectors. As a result, fluid flow between the patient and the interior of the IV bag is established.

In addition, known IV containers or reservoirs may incorporate an additional male or female connector disposed in fluid communication with a tube set or other type of conduit or delivery tubing. Additional male or female connectors of this type may be provided to administer additional liquid agents, such as pain medication, antibiotics, and/or other medicinal compositions, to the fluid being administered to the patient. However, such an additional male or female connector may remain unused or may be accessed subsequently to the initiation of the fluid administration, such as when additional medication or another composition is required or prescribed.

Therefore, there is a need in the medical field for an efficient, effective and easily applied closure assembly that would be capable of closing and sealing a male or female connector during periods of its non-use. Moreover, in order to detect and protect against non-authorized use, any such new closure assembly should preferably have tamper evident features, capable of providing a clear visual indication that use and/or non-authorized use has occurred. Accordingly, if any such tamper evident assembly were developed, it would preferably include a tamper evident cap structured to maintain a closed, sealed, tamper evident condition of the closed connector while being capable, through minimal structural modification, to be attached to a male or female connector associated with the fluid container or reservoir. If any such closure assembly were developed, it would preferably also be structured for efficient attachment to the connector associated with the reservoir in a manner which restricts or perhaps even stops fluid flow from the connector, and also the associated fluid reservoir to which it is attached. Any such tamper evident assembly developed would ideally also be structured to provide a clear indication whenever there has been tampering or other attempted access to the attached male or female connector and/or contents of the fluid reservoir or container associated with the male or female connector.

Additional features desirable in any such tamper evident assembly would include an ability to be used in combination with and connected to open ends of a medical conduit, tube set, etc. As such, the attached conduit or tube set could thereby be connected in direct fluid communication to the male or female connector associated with the fluid reservoir, by virtue of the interconnecting tamper evident assembly.

Finally, the structural components as well as the operational characteristics of any such proposed tamper evident assembly and associated tamper evident cap should ideally provide a sufficient degree of reliability relating to its intended use and function with a male or female connector to which it is attached, while restricting access and clearly indicating when access, including unauthorized access, thereto has occurred or been attempted.

SUMMARY OF THE INVENTION

The present invention is intended to present a solution to these and other needs, and accordingly, is directed to a tamper evident assembly which includes a tamper evident cap (TEC) that may vary in its structural configuration so as to be adaptable for use with a male connector or a female connector. In each of the different structural configurations, the TEC can be used in combination with a conduit, medical tube or "tube set" by being attached to at least one open end thereof. As explained in greater detail hereinafter, different tamper evident caps can be used to be attached to opposite open ends of the conduit, medical tube, etc.

In more specific terms, the TEC comprises an end cap having a substantially hollow configuration including one open end dimensioned and configured to receive the male or female connector. The end cap is preferably formed of a one-piece, integral construction including an open end and an integrated closed-end. In addition, the TEC also comprises a tip cap disposed within the interior of the end cap in an "operative position". When in such operative position, the tip cap is movable within and removable from the interior of the end cap. Further the tip cap is structured to be connected directly to the male or female connector, dependent on its structural configuration, when in the operative position. Accordingly, the structural features of the tip cap and its disposition in the aforementioned operative position defines a connection to the male or female connector with which the TEC is used. As will be explained in greater detail hereinafter, in at least some preferred embodiments of the tamper evident assembly of the present invention, the tip cap is disposed and structured to regulate fluid flow therethrough, and through the discharge opening or discharge port of the connector to which it is attached. As used herein, the tip cap and a flow controller thereof disposed to "regulate fluid flow" through the discharge port of a connector may be interpreted to mean either the prevention of such fluid flow, or in contrast, the establishment of a direct fluid flow or communication with the male or female connector, as well as the fluid reservoir, medical device, container, to which the male or female connector is attached.

Additional structural and operative features of the TEC include the provision of a retaining structure formed on the interior of the end cap, and a retention structure removably connected to the exterior of the tip cap. The cooperative disposition, configuration and overall structure of the retaining structure and the retention structure collectively define an operative interaction which facilitates disposition of the tip cap in its operative position within the interior of the end cap. In addition, such operative interaction between the retaining structure and the retention structure initially restricts removal of the tip cap from its operative position within the end cap.

In more specific terms, the operative interaction between the retaining structure and the retention structure results in an "interruptive engagement" which facilitates a uni-directional passage of the retention structure over the retaining structure when the tip cap is being disposed within the end cap, into the operative position. As indicated, the "interruptive engagement" is facilitated by the cooperative configuration, dimension and disposition of the retaining and retention structures. As suggested above, such interruptive engagement comprises a substantially sliding engagement of the retention structure over the retaining structure concurrent to disposition of the tip cap into the operative position. However, and in contrast, the interruptive engagement further comprises an "abutting engagement" of the retaining and retention structures, wherein such abutting engagement is preventative of passage of the retention structure over the retaining structure, concurrent to disposition of the tip cap out of its operative position and out of the interior of the end cap.

As a result, forced removal of the tip cap from its operative position within the interior of the end cap, such as when attached to a male or female connector, at least partially defines the "tamper evident" characteristics of the TEC. The retention structure is removably connected by one or more frangible members to the exterior of the tip cap. As a result, the forced removal of the tip cap from the interior of the end cap will result in the abutting engagement between the retaining and retention structures. In turn, this will result in a breakage of the one or more frangible members, and a detachment of the retention structure from the tip cap as it is being removed from its operative position within the end cap. Therefore, the retention structure will remain within the interior of the end cap, as the tip cap remains attached to the male or female connector while it is removed from the end cap. As a result, visual observation of the tip cap being attached to the connector of a reservoir or medical device on an exterior of the end cap, absent the presence of the retention structure, provides evidence of authorized or unauthorized use or access.

In various embodiments of the tamper evident assembly according to the present invention, the TEC includes a flow controller disposed on the interior of the tip cap. Also, a variance in the structural configuration of the tip cap may include structural modification of the flow controller so as to be disposed in fluid regulating relation with either a male connector or a female connector. As emphasized hereinafter, the disposition of the flow controller in "fluid regulating relation" to the attached male or female connector may include a prevention of fluid flow through the attached connector or an establishment of such fluid flow through the attached connector.

In addition, the various embodiments of the TEC may also include a one-way rotational drive structure, which may take the form of a modified "ramp and cliff" drive structure. The one-way rotational drive structure is thereby operative to prevent rotation of the tip cap relative to the end cap in one direction during a threaded or other attachment of the male or female connector to the tip cap. In contrast, the one-way drive assembly allows relative rotation of the tip cap and the end cap, thereby preventing the connector from being unthreaded from the tip cap, while the tip cap is in its operative position.

As set forth above, one or more additional embodiments of the tamper evident assembly includes a structural modification of the TEC, which allows it to be used in combination with a medical tube, conduit, tube set, etc. hereinafter collectively and independently referred to as a "conduit". The conduit is structured to include an interior lumen which in turn, defines a path of fluid flow to or from the TEC and the reservoir, container, medical device, etc. to which the aforementioned male or female connector is secured. Moreover, an open end of the conduit is connected within an interior of the tip cap in fluid communication with the flow controller thereof. The flow controller, whether structurally modified for use with a male or female connector, is further structured to define a "flow-through" configuration. Such a flow-through configuration establishes a path of fluid flow and direct fluid communication between the conduit and the male or female connector attached to the TEC, as well as the container, reservoir or medical device on which the male or female connector is secured. Further, in order to assure a stable fluid communication and/or path of fluid flow between the conduit and the male or female connector, through the TEC, the open end of the conduit is fixedly bonded, secured or attached within the interior of the tip cap.

The aforementioned modification of the structure of both the tip cap and the end cap to accommodate the use of the TEC with the conduit includes an apertured construction of the closed end of the end cap. Such an apertured construction allows the conduit, and at least a free end thereof, to extend through at least one aperture in the closed end into attachment with the interior of the tip cap. In addition, the flow controller may be structurally modified to define the aforementioned "flow-through configuration". Such a flow-through configuration differs from the flow controller having a substantially closed configuration to prevent fluid flow through the male or female connector, as well as the container, reservoir, with which the connector is operatively associated.

Accordingly, the structural components as well as the operational characteristics of the various embodiments of the tamper evident assembly of the present invention, as defined in greater detail hereinafter, will be operatively reliable for use with a male or female connector to which it is attached, while restricting access and clearly indicating when access, including unauthorized access, thereto has occurred or been attempted.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 3 is a perspective interior sectional view of the embodiment of FIGS. 1 and 2.

FIG. 4-A is a perspective view in exploded form of the tamper evident cap (TEC) shown in the embodiment of FIGS. 1 to 3 in a position to be attached to a female connector associated with a syringe or other reservoir.

FIG. 4-B is a perspective view of the tamper evident cap (TEC) shown in FIGS. 1-4A secured to a syringe.

FIG. 4-C is a perspective view in exploded form of the syringe of the embodiment of FIGS. 4A and 4B being detached from the tamper evident cap (TEC) in the embodiment of FIGS. 1-3.

FIG. 5 is a perspective view in exploded form of a tip cap positioned for assembly within an end cap of the tamper evident cap (TEC) of the embodiment shown in FIGS. 1 through 4-C.

FIG. 6 is a perspective, exploded view of the tip cap and TEC illustrated in FIG. 5.

FIG. 11 is a perspective view of another preferred embodiment of the tamper evident assembly incorporating a conduit or tube set being attached to one embodiment of a tamper evident cap of the tamper evident assembly of the present invention.

FIG. 12 is a perspective view in partial cutaway of one end of the conduit or tube set of the embodiment of FIG. 11, wherein the end cap and the tip cap are separated.

FIG. 13 is a perspective view in partial section and cutaway of one embodiment the tamper evident cap of the embodiment of FIGS. 11 and/or 12, being attached to one end of a conduit or tube set.

FIG. 16 is an exterior view of yet another embodiment of the tip cap having a male configuration and structurally configured for use with a conduit or tube set as represented in FIGS. 11-13.

FIG. 17 is a perspective interior view in longitudinal section of the embodiment of FIG. 16.

FIG. 18 is a perspective, longitudinal sectional view of the interior of another embodiment of the tamper evident cap, having a female configuration and associated with the tamper evident assembly of the present invention.

FIG. 19 is a perspective view in exploded form of yet another embodiment of a tamper evident cap, having a female configuration and structured for use with a conduit or tube set of the type represented in FIG. 11 and which may be associated with the tamper evident assembly of the present invention.

Like reference numerals refer to like parts throughout the several views of the drawings.

DETAILED DESCRIPTION OF THE PREFERRED EMBODIMENT

As represented in the accompanying drawings, the present invention is directed to a tamper evident assembly 200 including a tamper evident cap (TEC) 10 comprising both an end cap 12 and a tip cap 14, as is perhaps best illustrated in FIG. 5. Also, and as shown in FIG. 3, the tip cap 14 is positioned within the interior of the end cap 12 in an operative position. Moreover, the TEC is capable of being modified to assume different structural configurations which facilitate its operative attachment to either a male connector or a female connector, while the tip cap 14 is in the aforementioned operative position.

The structural and operative versatility of the tamper evident assembly 200, specifically including the TEC 10, also facilitate it having tamper evident capabilities. More specifically, the structural features of the TEC 10 provide a clear visual indication of an attempted use or access, either authorized or unauthorized, of a container, reservoir, medical device, etc. to which the male or female connector is attached, as demonstrated in more detail with reference to at least FIGS. 4-A through 4-C.

In addition, and with reference to FIG. 11, in one or more preferred embodiments of the tamper evident assembly 200, an at least minimal modification of the TEC 10 facilitate its use with medical tubing, conduit or a "tube set", generally indicated as 210 in FIGS. 11-13. For purposes of clarity the tubing, tube set, etc. 210 are collectively and independently referred to herein as "conduit". It is further noted that use of the TEC 10' with the conduit 210, as structurally modified in an appropriate manner, may be attached to either a male connector or a female connector, as represented in greater detail with specific reference to FIGS. 11-16.

Figure 1:
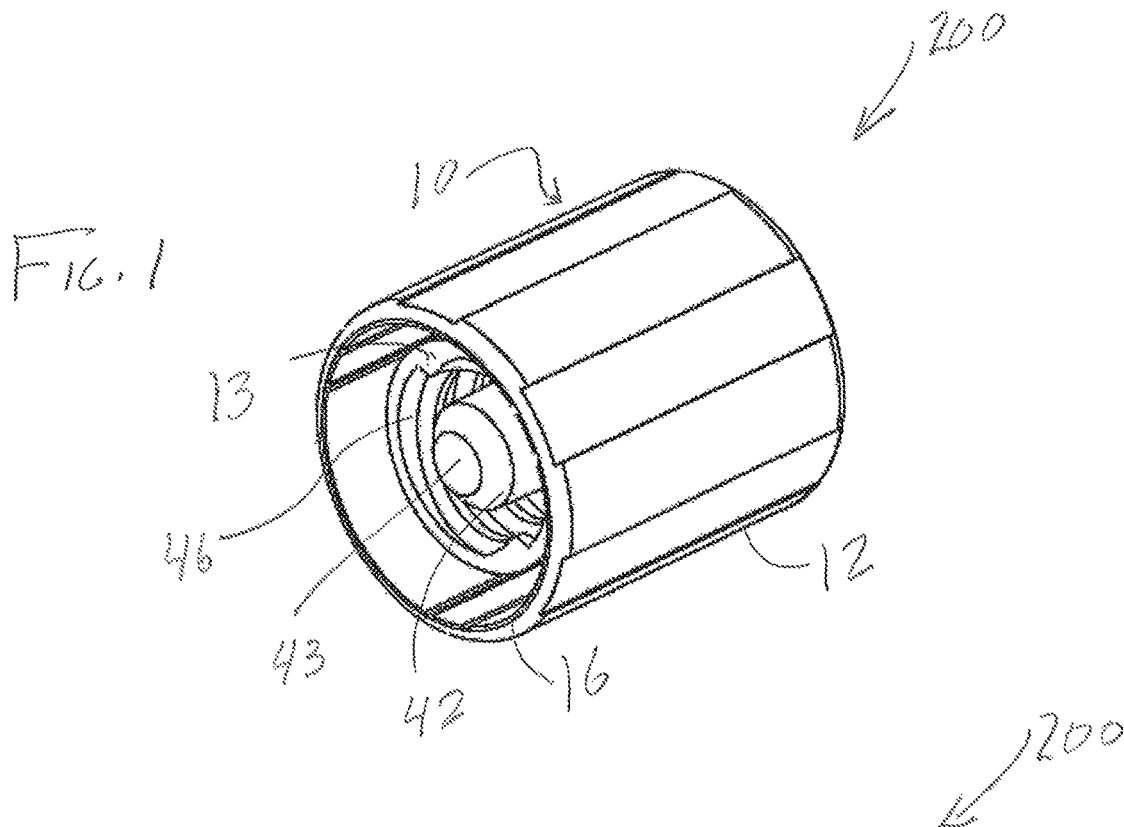
FIG. 1 is a perspective view of a tamper evident cap (TEC) having a male configuration and associated with the tamper evident assembly of the present invention.
Figure 2:
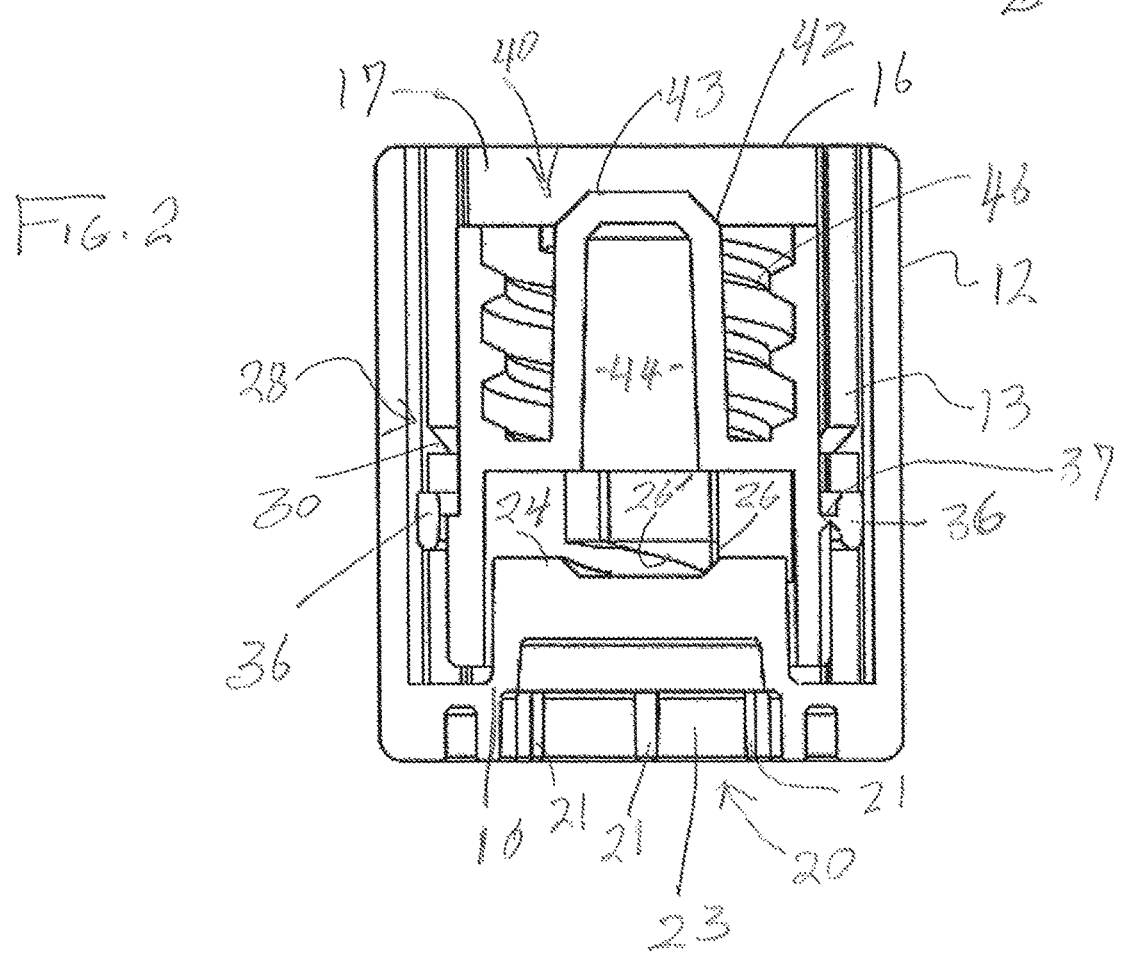
FIG. 2 is an interior sectional view of the embodiment of FIG. 1.

With initial reference now to FIGS. 1-10, and as represented in more specific detail in FIGS. 5-10, one preferred embodiment of the TEC 10 comprises the end cap 12 and the tip cap 14. The end cap 12 is preferably formed of a one-piece integral construction including an open end 16 providing direct access to the hollow interior 17. The open end 16 also facilitates positioning of the tip cap 14 into and out of its operative position, as represented in FIGS. 1-3, as well as facilitates access to the tip cap 14 when being attached to the male or female connector. The end cap 12 also includes a closed end 18 integrally formed with a remainder of the end cap 12 and having an exterior structure generally indicated as 20.

As disclosed in detail in what may be considered related intellectual property rights, namely, U.S. Pat. Nos. 8,591,462 and 9,199,749, issued respectively on Nov. 26, 2013 and Dec. 1, 2015 to Vitello, and assigned to the same corporate entity as the present application, the exterior 20 of the integrally formed, closed end 18 includes a plurality of projections 21, shown in FIGS. 2 and 3, formed at least partially on the interior peripheral surfaces of a corresponding recess 23. The plurality of projections 21 may vary in number and placement, but are cooperatively disposed, structured and dimensioned to interact with correspondingly structured and dimensioned projections of outwardly protruding connectors, which may be part of a package or packaging structure for a plurality of TECs 10 and/or 10'. Reference is specifically, but not exclusively made to FIGS. 8-10 and 11-14, of the above noted patents.

Figure 7:
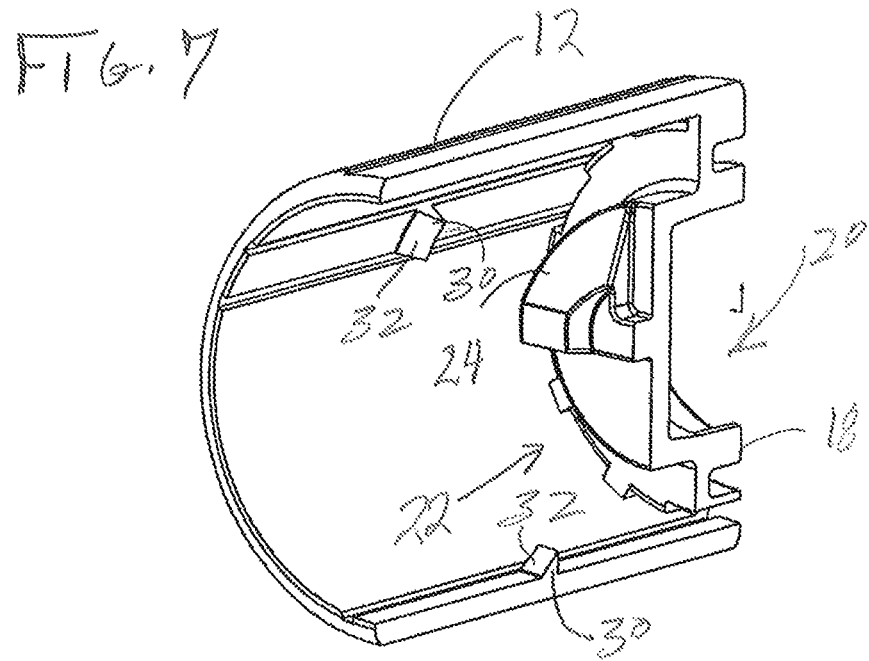
FIG. 7 is a perspective view in longitudinal section of the interior of the end cap of the embodiment of FIGS. 5 and 6.
Figure 8:
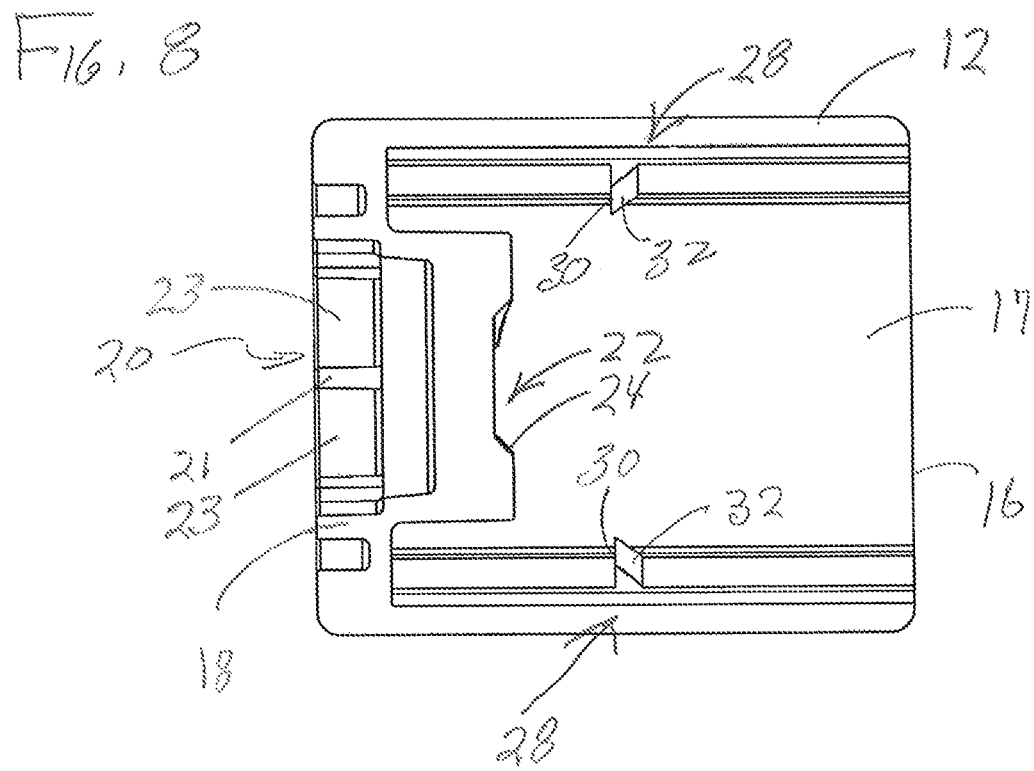
FIG. 8 is an interior sectional view of the embodiment of FIG. 7.
Figure 9:
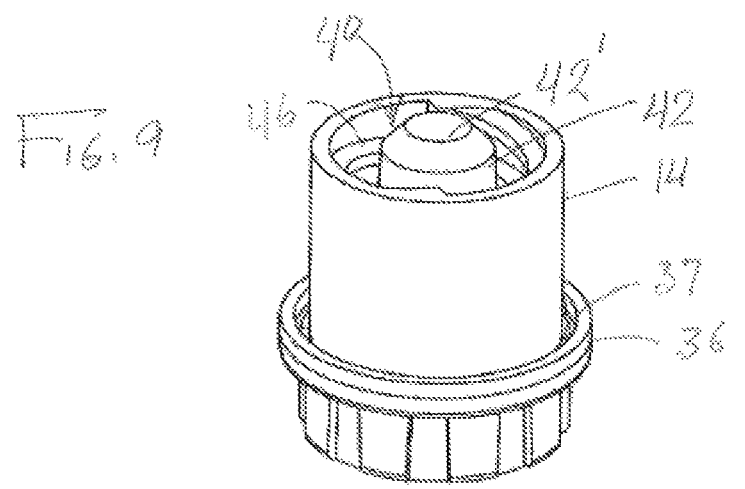
FIG. 9 is an exterior perspective view of the tip cap of the tamper evident cap of the embodiment of FIGS. 1-3.
Figure 10:
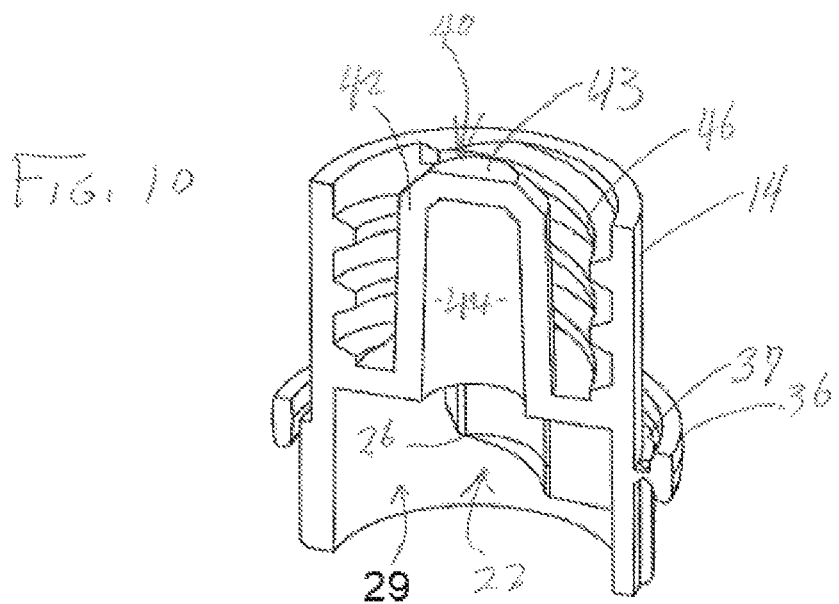
FIG. 10 is a perspective sectional view of the interior of the embodiment of FIG. 9.
Figure 14:
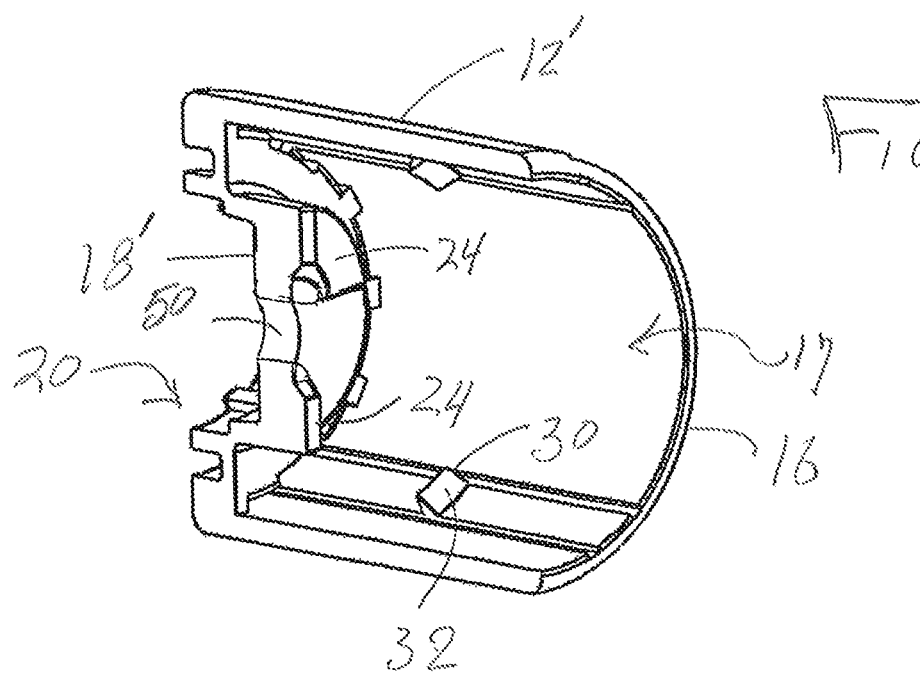
FIG. 14 is a perspective sectional view of the interior of another embodiment of the end cap which may be associated with the tamper evident cap structured for connection to a tube set or conduit as represented in the embodiment of FIGS. 11 and 12.
Figure 15:
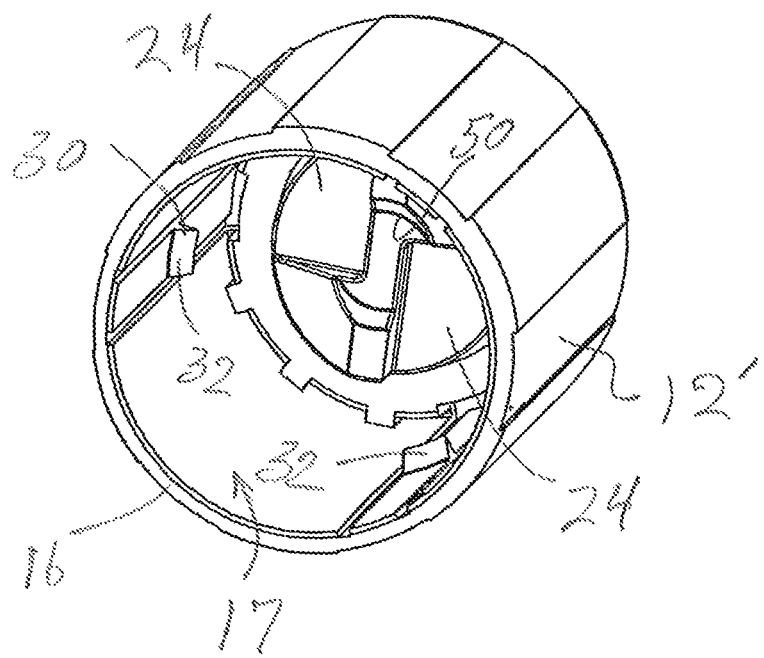
FIG. 15 is a perspective interior view in longitudinal section of the embodiment of FIG. 14.

As also represented in FIGS. 7 and 8, the interior surface of the closed end 18 includes a one-way rotational drive assembly, generally indicated as 22, in the form of a modified "ramp and cliff" drive assembly. The one-way rotational drive assembly 22 and/or ramp and cliff comprises a first drive segment 24 formed on the interior surface of the closed end 18. As referenced hereinafter, the one-way rotational drive assembly 22 also includes a second drive segment 26 formed on the interior sidewall of the tip cap 14, as clearly represented in at least FIGS. 3 and 10. As also indicated in greater detail, the structural and operative features of the rotational one way and/or ramp and cliff drive assembly 22 facilitates a threaded attachment of a connector, as at 200 in FIG. 4A, with the tip cap 14 while preventing an unthreading thereof.

Additional features of the TEC 10, and in particular, the end cap 12, include a retaining structure generally indicated as 28. The retaining structure 28 comprises at least one, but preferably a plurality of retaining members 30 disposed within the end cap 12, preferably on the interior surface thereof. In addition, the plurality of retaining members 30 are disposed in laterally spaced relation to one another so as to collectively and at least partially, surround the exterior of the end cap 14, when the end cap 14 is disposed in the operative position of FIGS. 1-3. It is further noted that each of the one or more retaining members 30 are disposed, dimensioned and configured to facilitate passage of the tip cap 14 into the interior 17 of the end cap 12, through the open end 16 thereof and into its operative position. In contrast, the disposition, dimension, configuration and overall structuring of the retaining structure 28, and in particular, the one or more retaining members 30 restricts removal of the tip cap 14 from its operative position and out of the end cap 12, as generally represented in FIG. 4-C. In the illustrated embodiment represented throughout the accompanying Figures, the retaining structure 28, including the one or more retaining members 30, have a preferred configuration, which includes, but is not limited to, an angled, beveled, chamfered, etc. face or end portion 32, which faces outwardly from the interior 17 end cap 12 towards the open end 16.

It is emphasized that the specific disposition and overall structure of the one or more retaining members 30 may differ in size, placement and even configuration. As such, the one or more retaining members 30 may comprise elongated flanges or rib structures, having a curvilinear configuration which conforms to the interior surface portion(s) of the end cap 12 to which they are secured or connected.

With reference now to FIG. 2, in order to efficiently accomplish the intended operative interaction between the end cap 12 and the tip cap 14, which facilitates the tip cap 14 being disposed into its operative position, a retention structure, generally indicated as 36, is mounted on or connected to the exterior of the tip cap 14. More specifically, and as shown in FIG. 3, the retention structure 36 comprises a substantially circular or annular ring or similar structure connected to and extending at least minimally outward from the exterior surface of the tip cap 14. As such, the retention structure 36 may be in the form of a continuous ring or otherwise be at least partially segmented into a plurality of ring or rib segments (not shown), which individually or collectively are disposed in at least partially or completely surrounding relation to the exterior of the tip cap 14. The least partially surrounding relation of the retention structure 36 to the exterior of the tip cap 14 facilitates its "interruptive engagement" with the retaining structure 28 and the one or more of the plurality of retaining members 30. Additional structural and operative features of the retention structure 36 includes it being structured or disposed to have at least a minimal amount of flexure or flexibility. Such flexible characteristics may be attributed to its outward spacing from the exterior surface of the tip cap 14 and/or its removable connection thereto by a plurality of frangible members 37 and/or the forming of at least a portion of the retention structure 36 from an at least partially flexible material.

Therefore, the cooperative structuring, disposition and dimensioning of the retaining structure 28 and the retention structure 36 defines the aforementioned "interruptive engagement" with one another as the tip cap 14 passes into its operative position within the interior 17 of the end cap 12, as well as when it passes out of its operative position, through the open end 16, to an exterior of the end cap 12. Generally, such interruptive engagement defines a facilitated passage of the tip cap 14, with the retention structure 36 attached thereto, into its operative position. In contrast, the occurrence of such interruptive engagement at least partially restricts removal of the tip cap 14 from its operative position and in doing so prevents removal of the retention structure 36.

In more specific terms, the aforementioned interruptive engagement comprises a substantially sliding engagement of the retention structure 36 over the retaining structure 28, including the one or more retaining members 30, concurrent to disposition of the tip cap 14 through the open end 16 and into its operative position. In contrast, the interruptive engagement further comprises an "abutting engagement" of the retention structure 36 with the one or more retaining members 30 of the retention structure 28. More specifically, as the tip cap 14 is forcibly removed from the interior 17 of the end cap 12. The "abutting engagement" between the retainer structure 28 and the retention structure 36 is preventative of passage of the retention structure 36 over the one or more retaining members 30 of the retaining structure 28. Such "abutting engagement" further results in a breakage or fracture of the plurality of frangible members 37 serving to removably interconnect the retention structure 36 to the exterior surface of the tip cap 14. Therefore, upon breakage of the frangible members 37 and due to the abutting engagement, the retention structure 36 will be removed from the exterior of the tip cap 14 and remain captured within the interior of the end cap 12. A continued removal force, as schematically represented as 300 in FIG. 4C, being exerted on the tip cap 14 will result in its removal from the interior 17 of the end cap 12, such as when it is attached to a connector 201 of a syringe such as shown in FIG. 4A or other medical device 206.

As disclosed in detail in the embodiments of the accompanying Figures, the predetermined cooperative configuration of at least the plurality of retaining members 30, including the angled, beveled and/or chamfered faces 32, facilitate the aforementioned sliding engagement of the retention structure 36 over the plurality of retaining members 30. Moreover, the structural flexure or flexible capabilities of the retention structure 36, as set forth above, will allow it to be at least minimally flexed inwardly, towards the portion of the tip cap 14 to which it is attached. Such inward flexure of the retention structure 36 occurs as it engages the chamfered faces 32. Such interactive, "interruptive engagement" between the retention structure 36 and the chamfered faces 32 results in the aforementioned "sliding engagement" therebetween, as the tip cap 14 is placed or disposed into its operative position within the end cap 12, from an exterior thereof. Further, once the retention structure 36 passes over and beyond the chamfered surfaces 32 it will assume its normal, original outwardly expanded orientation, due in part to its flexible characteristics, as set forth above. As such the placement or positioning of the tip cap 14 into its operative position within the interior 17 of the end cap 12 may be accurately referred to as a "snap-fit" insertion. Such a "snap-fit" connection will, as should be apparent, be the result of the retention structure 36 assuming its normal, original, outwardly expanded orientation, subsequent to engaging the plurality of retaining members 30.

As represented in at least FIGS. 1-3, 9 and 10, the structural configuration of the tip cap 14 is that of a female connector dimensioned and structured to receive a female connector, as at 201 in FIG. 4A. Accordingly, the tip cap 14 additionally includes a flow controller 40 integrally or otherwise appropriately secured on the interior thereof. In the female connector of the indicated Figures, the flow controller 40 comprises a generally elongated, outwardly projecting plug 42, which may also include an open or hollow interior disposed in direct communication with an additional open interior 29 of the tip cap 14. The opposite end of the plug 42 of the flow controller 40 is closed as at 42' in order to prevent or restrict fluid flow through the female connector 201 to which it is attached.

In more specific terms, and again with primary reference to FIGS. 4A-4C, the TEC 10 is pre-assembled as represented in FIG. 4A and is ready for attachment to the female connector 201 of a container, reservoir, medical device, etc. such as a prefilled syringe 202. A threaded interconnection occurs therebetween due to the internal threads 46 formed on the interior of the tip cap 14, in at least partially surrounding relation to the plug 42. These internal threads or corresponding threaded surface 46 will mate by threaded engagement with the threads or outwardly extending ribs or ears 206 formed on the female connector 201. Upon connection, the closed end 42' and at least a portion of the plug 42 will pass into the discharge port or opening 204 of the connector 201, thereby restricting or preventing fluid flow into or out of the discharge port 204 and the female connector 201.

With primary reference to FIG. 4-C, use or access to the container, reservoir and/or syringe 202 and/or the contents thereof, is typically accomplished by removal of the tip cap 14 from the female connector 201. However, the provision of the aforementioned uni-directional, rotational ramp and cliff drive assembly 22 prevents the female connector 201 from being unthreaded from the fluid restricting engagement with the flow controller 40. In more specific terms, the first drive segment 24 formed on the interior surface of the closed end 18 and the second drive segment 26 formed on the interior sidewall surface of the tip cap 14 are cooperatively configured and disposed to prevent relative rotation of the tip cap 14 and the end cap 12 in one direction but allow relative rotation thereof in an opposite direction. As represented in FIG. 3, the threading of the female connector 201 onto the flow controller 40 will most probably result in a clockwise direction of rotation of the female connector 201 so as to cause a threaded engagement between the interior threaded portion 46 and the exterior ribs, ears or thread members 206 on the female connector 201. This clockwise direction of rotation will, in turn, cause the tip cap 14 to also rotate in a clockwise direction within the interior 16 of the end cap 12. As a result, the second drive segment 26 will engage a raised portion of the first drive segment 24. Such engagement will prevent relative rotation between the tip cap 14 an end cap 12 in a clockwise direction. As a result, the female connector 201 will be able to continue a clockwise direction of rotation and be threaded onto the flow controller 40. However, due to the slanted, sloped peripheral portion 26' of the second drive segment 26 and the cooperative disposition and configuration of the first drive segment 24, the rotation of the tip cap in the opposite or counter-clockwise direction will not be prevented. Such reversed or counter-clockwise direction of rotation will not be prevented due to the sliding engagement between the slanted periphery 26' and the portions of the first drive segment 24 which it engages. As a result, the connector 201 will not be able to be unthreaded from the tip cap 14.

Therefore, the only practical way of accessing the connector 201 would be to exert an outwardly directed pulling force or otherwise appropriate directional force 300, as schematically represented in FIG. 4-C, on the tip cap 14 while it is connected to the female connector 201. Such an outwardly directed pulling or other appropriate force 300 will result in the aforementioned interactive, abutting engagement of the retention structure 36 with the retaining structure 28. As stated herein, such an abutting engagement will result in a detachment of the retention structure 36 from the exterior of the tip cap 14, as the tip cap 14 is removed from its operative position within the interior 17 of the end cap 12. The retention structure 36 will remain captured within the interior 17 of the end cap 12 and the tip cap 14 will remain connected to the female connector 201, as represented in FIG. 4C. Moreover, upon removal from the end 12, the tip cap 14 will be visually observable without the retention structure 36 (also referred to as an indicator ring) being attached thereto. Therefore, a visual indication of attempted or actual use, whether authorized on unauthorized will be evident.

Yet another preferred embodiment of the tamper evident assembly 200 is represented in FIGS. 11-17. As set forth above, the tamper evident assembly 200 comprises a tamper evident cap (TEC) 10' which is structurally adapted to be used with a medical conduit 210. As with the embodiment of the TEC 10, the TEC 10' may also be structurally adapted for attachment to a female connector 201, of the type represented in FIG. 4A, or a male connector. Moreover, the TEC 10' includes many of the structural features present in the TEC 10 as described above. Such common structural features include end cap 12', tip cap 14', a one-way rotational drive assembly 22, preferably in the form of a ramp and cliff; a retaining structure 28 and a retention structure 36.

However, modified structural features of the TEC 10' further include a flow controller 40' structured for attachment to a female connector by virtue of a threaded surface area 46. As such, the flow controller 40' includes an outwardly extending plug 42' disposable in fluid regulating relation within the interior of a discharge opening or discharge port 204 as represented in FIG. 4A. The modifications of the TEC 10' further include the structuring of the flow controller 40' to have a "flow-through" construction or configuration comprising an open end 43' disposed in direct fluid communication with the hollow, open interior 44 of the flow controller/plug 40', 42'. Further structural features of the TEC 10' include the fixed attachment and/or bonded connection of an open end 210' of the conduit 210 within the interior of the tip cap 14'. Such a fixed, bonded connection assures the stability of a path of fluid flow through the interior lumen of the conduit 210 and into the interior of the tip cap 14' so as to be in direct fluid communication with the "flow-through" structure of the flow controller 40'. The fixed, bonded connection between the open end 210' of the conduit 210 may be accomplished by a sleeve or receiving channel 48 integrally or otherwise fixedly disposed within the interior of the tip cap 14' as clearly represented FIG. 13. The sleeve or receiving channel 48 is disposed in direct fluid communication with the interior of the flow controller 40' and more specifically, with the interior 44 of the plug 42'.

Positioning of the open end 210' in fixed attachment within the interior of the tip cap 14' is accomplished by passage of the open end 210' and at least a portion of the remainder of the conduit 210, through the closed end 18' of the end cap 12'. Such passage is facilitated by the closed end 18' having an apertured construction at least partially defined by at least one opening 50 formed in the closed end 18'. The opening or aperture 50 is disposed, dimensioned and configured to facilitate passage of the open end 210', as well as an adjacent or adjoining portion of the conduit 210, through the closed end 18' and into the fixed, bonded engagement with the receiving, mounting channel 48. As such, the path of fluid flow within the interior of the conduit 210 is disposed in direct fluid communication with the interior of the "flow-through" flow regulator 40', as clearly represented in FIG. 13.

As represented in FIG. 11, different ones of the TEC 10' may be operatively connected to opposite open ends 201' of the conduit 210. Accordingly, the structural and operative features represented in FIGS. 12 and 13 are presented to indicate the structural and operative features of each of the TECs 10' being attached to different ones of the open ends of the conduit 210.

As emphasized herein, the tamper evident assembly 200 of the present invention includes a tamper evident cap (TEC) which may be structurally modified to assume either a male configuration, as represented in FIGS. 1-17, or a female configuration as represented in FIGS. 18 and 19. Accordingly, for purposes of clarity, the TEC having the female configuration is generally indicated as 110 and is structurally adapted to be incorporated within the tamper evident assembly 200 of the present invention, independent of connection to the conduit or tube set 210. In a further embodiment and/or structural modification, the TEC is generally represented as 210' and includes the aforementioned flow through construction enabling it to be operatively bonded or otherwise fixedly connected to an open end 210' of the conduit or tube set 210, as described herein with reference to the embodiment of FIG. 13.

It should also be apparent that many of the structural features and components of the TEC 10 and/or 10', having the male configuration, are incorporated in the TEC 110 and/or 110' which has the female configuration. Further, it is emphasized for purposes of clarity and in order to avoid repetitive descriptive details, these common structural features and components are represented as having the same reference numerals in the embodiments of FIGS. 1-17 and the embodiments of FIGS. 18 and 19. However, due to the male configuration of the embodiments of FIGS. 1-17, different structural features exist in the embodiment of FIGS. 18 and 19 due to its female configuration.

In more specific terms, and with primary reference now to FIGS. 18 and 19, the TEC 110 is structured for use independent of a conduit or tube set 210 of the type represented in FIGS. 11-13.

As such, the TEC 110 is absent the aforementioned flow through construction and includes a flow controller 140 in the form of an open chamber 142 having an open outer end 143. In addition, thread segments or ribs 146 are formed on the exterior of the flow controller 140 and are disposed to engage in a threaded, mating relation with a corresponding threaded surface on a male connector which may be associated with a nozzle or discharge port of a syringe of the type represented in FIGS. 4A-4C. More in particular, such a male connector may be formed on and be structurally and operatively associated with a nozzle or discharge port of a syringe, such as of the type of syringe 202, represented in FIGS. 4A-4C. Moreover, the open chamber 142 of the flow controller 140 is disposed, dimensioned and configured to receive the nozzle or discharge port of such a male connector, in the open interior chamber 142, concurrently to the ribs or thread segments 146 engaging corresponding threaded surfaces of the male connector. Accordingly, such interaction between the nozzle or discharge port of a male connector of a syringe being disposed within the open interior chamber 142 of the flow controller 140 will restrict the flow of fluid through the male connector of the syringe connected to the TEC 110.

With primary reference now to FIG. 19, the TEC 110' is structurally modified from that of the TEC 110 of FIG. 18 and is representative of yet another preferred embodiment of the tamper evident assembly 200 of the present invention. More specifically, the TEC 110' includes the aforementioned flow through configuration and facilitates connection to the open end 210' of a conduit or tube set 210. As such, the open end 210' and adjacent portions conduit 210 may pass through the opening or aperture 50 defining an apertured construction of the integral closed end 18' of the end cap 112'. This is substantially equivalent to the apertured construction of the end cap 12' represented in the embodiment of the TEC 10' in FIGS. 14 and 15. In addition, an open end 210' of the conduit or tube set 210 is bonded and/or fixedly secured on the interior 29 of the tip cap 114'. Further, an opening or aperture 143' is formed in a normally segregating partition 145 at the bottom or base end of the open interior chamber 142 of the flow controller 140. This opening 143' establishes direct fluid communication between the open end 210' of the conduit or tube set 201 and any male configured nozzle or discharge port of a syringe or other container disposed within the open interior chamber 142. A further structural adaptation of the embodiment of FIG. 19 may include a similar connecting sleeve 48, as represented in FIG. 13, to facilitate the fixed attachment or bonding of the open end 210' on the interior of the tip cap 114'.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A tamper evident assembly structured for attachment to a medical connector, said tamper evident assembly comprising:
    a tamper evident cap including an end cap and a tip cap, said tip cap movably and removably disposed in an operative position within said end cap,
    a retaining structure disposed on an interior surface of said end cap in retaining relation to said tip cap,
    said tip cap including a retention structure removably connected to an exterior of said tip cap,
    said retaining structure disposed in removal preventing relation to said retention structure concurrent to said tip cap being in said operative position,
    said retaining structure and said retention structure cooperatively structured and configured to define a substantially sliding engagement therebetween concurrent to passage of said tip cap from an exterior of said end cap into said operative position, and
    said substantially sliding engagement comprises a flexure of at least one of said retaining structure and retention structure relative to the other one of said retaining structure and retention structure, concurrent to said passage of said tip cap into said operative position.

2. The tamper evident assembly as recited in claim 1 wherein said retaining structure comprises a predetermined configuration, at least partially facilitating said substantially sliding engagement; said predetermined configuration defining a unidirectional passage of said retention structure over said retaining structure.

3. The tamper evident assembly as recited in claim 2 wherein said unidirectional passage is concurrent to said passage of said tip cap into said operative position.

4. The tamper evident assembly as recited in claim 2 wherein said predetermined configuration defines an abutting engagement of said retaining structure with said retention structure, said abutting engagement preventative of said substantially sliding engagement and passage of said retention structure over said retaining structure, concurrent to disposition of said tip cap out of said operative position.

5. The tamper evident assembly as recited in claim 2 wherein said predetermined configuration comprises a chamfered shape of at least a portion of said retaining structure.

6. The tamper evident assembly as recited in claim 5 wherein said chamfered shape is disposed on said retaining structure in an outwardly facing relation to an open end of said end cap.

7. The tamper evident assembly as recited in claim 2 wherein said retaining structure comprises at least one retaining segment formed on and extending outwardly from an interior surface of said end cap in interruptive engagement with said retention structure.

8. The tamper evident assembly as recited in claim 7 wherein said retaining structure comprises a plurality of retaining segments formed on and extending outwardly from said interior surface; said plurality of retaining segments disposed in laterally spaced relation to one another.

9. The tamper evident assembly as recited in claim 7 wherein said retention structure is disposed in at least partially surrounding relation to an exterior surface of said tip cap.

10. The tamper evident assembly as recited in claim 9 wherein said at least one retaining segment and said retention structure respectively extend outwardly from an inner surface of said end cap and an outer surface of said tip cap into said interruptive engagement with one another upon disposition of said tip cap into and out of said operative position.

11. The tamper evident assembly as recited in claim 9 wherein said interruptive engagement defines a detachment of said retention structure from said tip cap concurrent to passage of said tip cap out of said operative position.

12. The tamper evident assembly as recited in claim 11 wherein said interruptive engagement defines a sliding engagement of said retention structure over said retaining structure concurrent to disposition of said tip cap into said operative position.

13. A tamper evident assembly structured for attachment to a medical connector, said tamper evident assembly comprising:
    a tamper evident cap including an end cap and a tip cap, said tip cap movably and removably disposed in an operative position within said end cap,
    a retaining structure disposed on an interior surface of said end cap in retaining relation to said tip cap,
    said tip cap including a retention structure removably connected to an exterior of said tip cap,
    said retaining structure disposed in removal preventing relation to said retention structure concurrent to said tip cap being in said operative position, and
    said retaining structure and said retention structure cooperatively structured and configured to define a substantially sliding engagement therebetween concurrent to passage of said tip cap from an exterior of said end cap into said operative position.

14. The tamper evident assembly as recited in claim 13 further comprising a flow controller formed within the said tip cap; said flow controller disposed to engage and at least partially regulate fluid flow through the medical connector.

15. The tamper evident assembly as recited in claim 14 wherein said flow controller comprises a predetermined configuration structured to regulate fluid flow through a female medical connector.

16. The tamper evident assembly as recited in claim 15 wherein said predetermined configuration of said flow controller comprises a plug dimensioned and configured to extend into a discharge port of the female connector.

17. The tamper evident assembly as recited in claim 14 wherein said flow controller comprises a predetermined configuration structured to regulate fluid flow through a male medical connector.

18. The tamper evident assembly as recited in claim 17 wherein said flow controller comprises a chamber dimensioned and configured to receive a discharge port of the male connector therein.

19. A tamper evident assembly structured for attachment to a medical connector, said tamper evident assembly comprising:
    a tamper evident cap including an end cap and a tip cap, said tip cap movably and removably disposed in an operative position within said end cap, a retaining structure disposed on an interior of said end cap in retaining relation to said tip cap; said tip cap including a retention structure removably connected to an exterior thereof, at least one of said retaining structure and said retention structure comprising a predetermined configuration, said predetermined configuration defining a unidirectional passage of said retention structure over said retaining structure, said predetermined configuration and relative dispositions of said retaining structure and said retention structure collectively defining an interruptive engagement with one another upon disposition of said tip cap into and out of said operative position, said interruptive engagement comprising a substantially sliding engagement of said retention structure over said retaining structure concurrent to disposition of said tip cap into said operative position, said interruptive engagement further comprising an abutting engagement of said retaining structure with said retention structure, said abutting engagement preventative of passage of said retention structure over said retaining structure, concurrent to disposition of said tip cap out of said operative position, and a flow controller formed within the said tip cap and disposed to engage and at least partially regulate fluid flow through the medical connector, when attached to said tamper evident cap.

20. The tamper evident assembly as recited in claim 19 further comprising a conduit having an open end connected within an interior of said tip cap in fluid communication with said flow controller.

21. The tamper evident assembly as recited in claim 20 wherein said flow controller comprises an open, flow-through configuration disposed to establish a path of fluid flow, through said open end, between an interior of said conduit and the connector attached to said tamper evident cap.

22. The tamper evident assembly as recited in claim 21 wherein said flow controller comprises a predetermined configuration structured to regulate fluid flow through a male medical connector.

23. The tamper evident assembly as recited in claim 22 wherein said predetermined configuration of said flow controller comprises a plug dimensioned and configured to extend into a discharge port of the female connector.

24. The tamper evident assembly as recited in claim 21 wherein said flow controller comprises a predetermined configuration structured to regulate fluid flow through a male medical connector.

25. The tamper evident assembly as recited in claim 24 wherein said flow controller comprises a chamber dimensioned and configured to receive a discharge port of the male connector therein.

26. The tamper evident assembly as recited in claim 20 wherein said open end is fixedly connected within said tip cap, concurrent to said tip cap being in said operative position.

27. The tamper evident assembly as recited in claim 26 wherein said at least one free and extends through said end cap and into fixed connection within said interior of said tip cap.

28. The tamper evident assembly as recited in claim 26 wherein said end cap includes a closed end having an apertured construction structured to receive said conduit, said open end disposed through said apertured construction of said closed end into said fixed connection with said interior of said tip cap.

29. The tamper evident assembly as recited in claim 28 wherein said closed and is integrally connected to a remainder of said end cap.

30. The tamper evident assembly as recited in claim 28 further comprising a unidirectional drive assembly including a first drive segment disposed on said end cap and a second drive segment disposed on said tip cap; said first and second drive segments disposed in interactive engagement, said interactive engagement defining relative rotation between said end cap and said tip cap restricted to a single direction.

31. A tamper evident assembly as recited in claim 30 wherein said first and second drive segments are respectively disposed on an inner surface of said closed end of said end cap and on an inner sidewall surface of said tip cap.

* * * * *